(12) United States Patent
Fleming, III et al.

(10) Patent No.: US 6,302,852 B1
(45) Date of Patent: Oct. 16, 2001

(54) BONE MARROW BIOPSY DEVICE

(75) Inventors: James A. Fleming, III, Buffalo Grove; Werner Mittermeier, Prospect Heights, both of IL (US)

(73) Assignee: Manan Medical Products, Inc., Northbrook, IL (US)

( * ) Notice: Subject to any disclaimer, the term of this patent is extended or adjusted under 35 U.S.C. 154(b) by 0 days.

(21) Appl. No.: 09/557,815

(22) Filed: Apr. 25, 2000

(51) Int. Cl.[7] ........................................ A61B 5/00
(52) U.S. Cl. ............................................... 600/567
(58) Field of Search ........................... 600/562, 564–567; 606/167, 170

(56) References Cited

U.S. PATENT DOCUMENTS

| | | | |
|---|---|---|---|
| 3,844,291 | 10/1974 | Moen | 128/354 |
| 4,403,617 | 9/1983 | Tretinyak | 128/754 |
| 4,630,616 | 12/1986 | Tretinyak | 128/753 |
| 4,651,752 | 3/1987 | Fuerst | 128/754 |
| 4,655,226 | 4/1987 | Lee | 128/754 |
| 4,785,826 | 11/1988 | Ward | 128/754 |
| 4,838,282 | 6/1989 | Strasser et al. | 128/754 |
| 5,074,311 | 12/1991 | Hasson | 128/754 |
| 5,148,813 | 9/1992 | Bucalo | 128/754 |
| 5,172,700 | 12/1992 | Bencini et al. | 128/751 |
| 5,286,255 | 2/1994 | Weber | 604/22 |
| 5,318,589 | 6/1994 | Lichtman | 606/205 |
| 5,333,619 | 8/1994 | Burgio | 128/754 |
| 5,357,974 | 10/1994 | Baldridge | 128/754 |
| 5,462,062 | 10/1995 | Rubinstein et al. | 128/754 |
| 5,522,398 | 6/1996 | Goldenberg et al. | 128/754 |
| 5,595,186 | 1/1997 | Rubinstein et al. | 128/754 |
| 5,634,473 | 6/1997 | Goldenberg et al. | 128/754 |

*Primary Examiner*—Max Hindenburg
(74) *Attorney, Agent, or Firm*—Dick & Harris

(57) ABSTRACT

The present invention is directed to a bone marrow biopsy needle including an outer cannula having a proximal end, a distal end, a hollow section therebetween and a handle portion associated with the proximal end, and an inner rod having a proximal end, a distal end and a handle cap. The handle portion further includes a grip enhancement member which is formed from a material distinct from at least a portion of the handle portion, such as rubber. The grip enhancement member may take the form of insert members which fit into cavities in the handle portion of the outer cannula. The grip enhancement member not only enhances the gripping surface of the bone marrow biopsy needle, but also provides cushioning for a user and adds weight to the handle portion to facilitate weight distribution throughout the outer cannula handle.

19 Claims, 2 Drawing Sheets

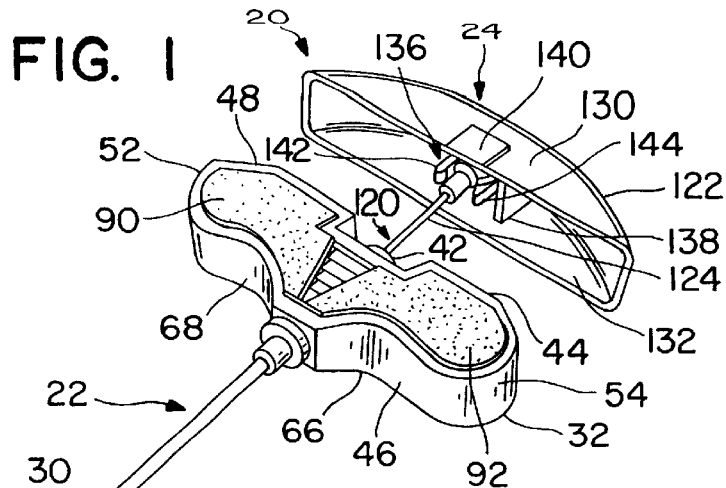
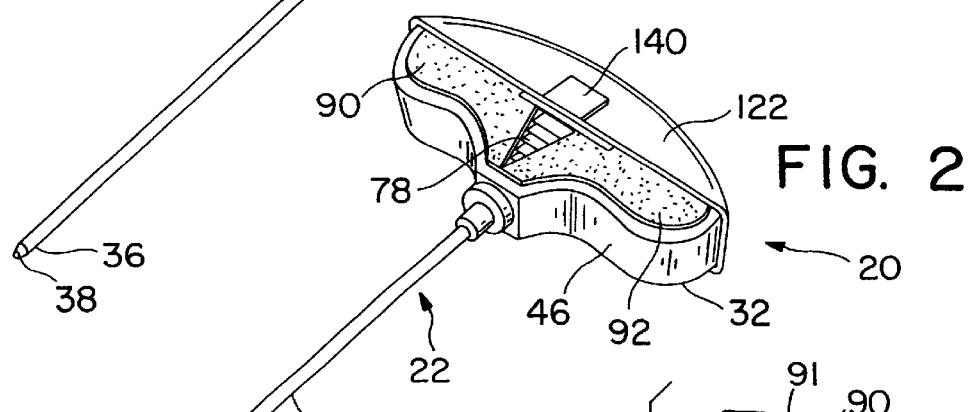
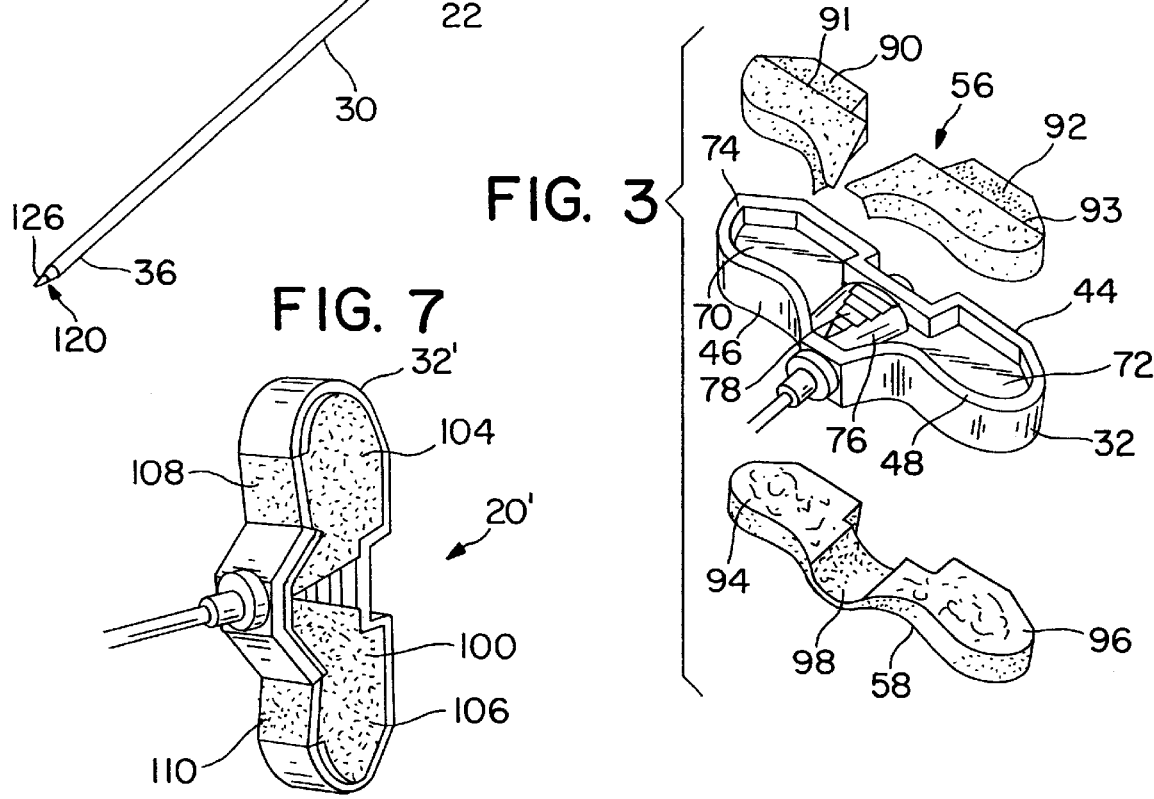
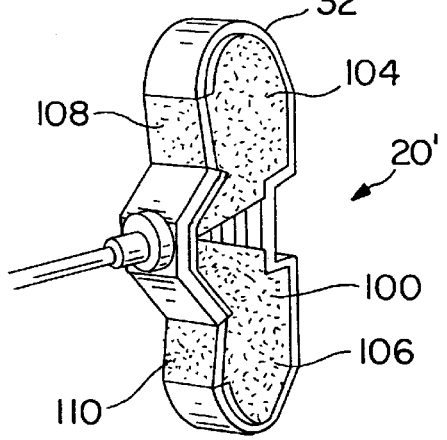

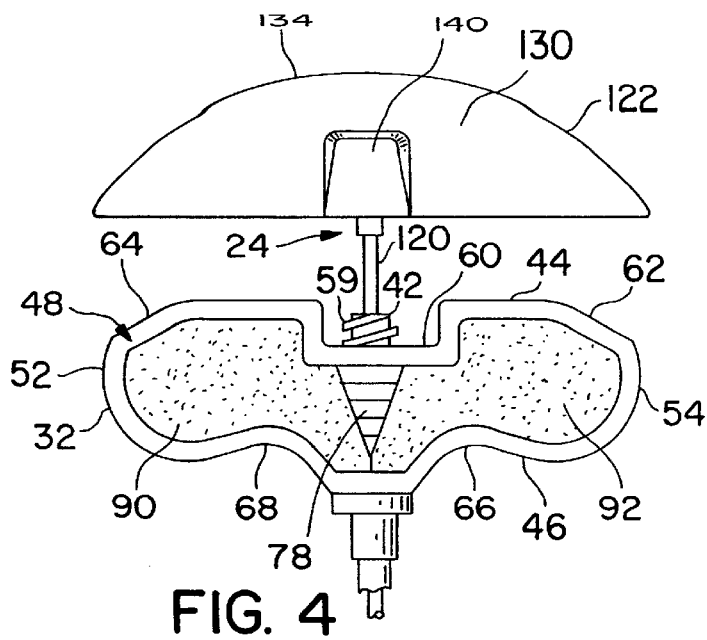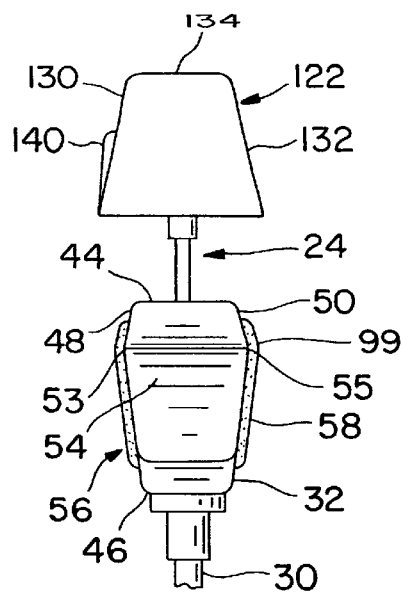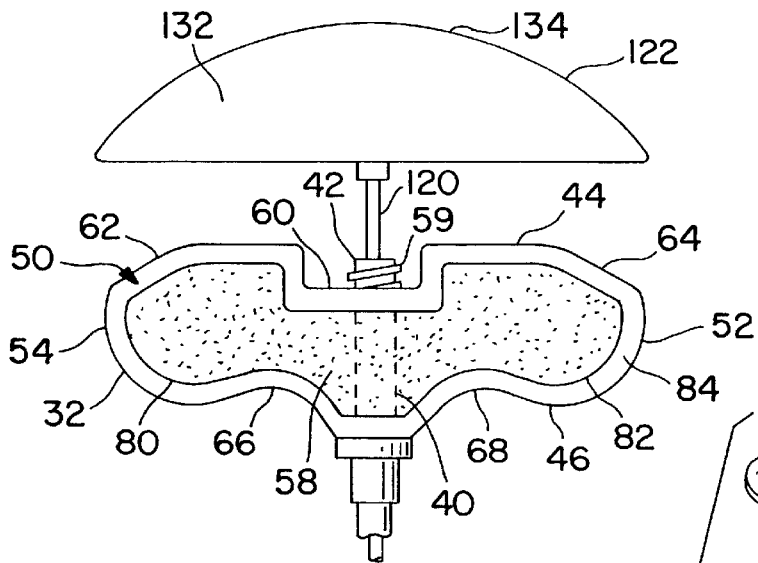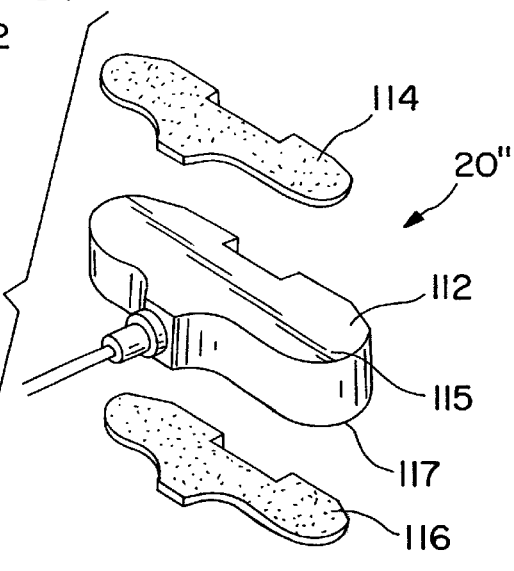

BONE MARROW BIOPSY DEVICE

BACKGROUND OF THE INVENTION

1. Field of the Invention

The present invention relates in general to bone marrow biopsy devices and, more particularly, to a bone marrow biopsy device with a grip enhancement feature.

2. Background Art

Bone marrow biopsy devices have been known in the art for many years. In particular, many bone marrow biopsy devices have included a hollow outer cannula with some form of inner rod slidable within the outer cannula. The outer cannula conventionally consists of a proximal end, a distal end and some form of a handle associated with the proximal end. The inner rod may typically take several different forms, including a sharpened stylet for insertion of the bone marrow biopsy needle into a patient, an inner cannula for sampling bone marrow, and/or an ejector rod for forcing the sample out of the outer cannula. The inner rod also typically includes a second or connection handle which may be secured to the handle portion of the outer cannula.

For instance, Baldridge, U.S. Pat. No. 5,357,974, Tretinyak, U.S. Pat. No. 4,403,617, Tretinyak, U.S. Pat. No. 4,630,616, Lee, U.S. Pat. No. 4,655,266 and Strasser et al., U.S. Pat. No. 4,838,282 all disclose bone marrow biopsy devices having a first handle mounted on the outer cannula and a second handle mounted on the inner rod. The first and second handle portions of these devices are constructed from the same material, typically a light weight plastic. Moreover, these handles are usually designed to securably mate with one another, for instance by a locking member, such as that taught in Mittermeier et al., Ser. No. 09/137,854, incorporated herein by reference.

Additionally, several of these bone marrow biopsy devices have included handle features which enhance the ability of a user to both grip and manipulate the bone marrow biopsy needle. For instance, Strasser, U.S. Pat. No. 4,838,282 discloses finger grooves in the outer cannula handle portion, while Tretinyak, U.S. Pat. No. 4,403,617 discloses ridges on both the first and second handle portions to facilitate a users grasping of the device.

Although these and other bone marrow biopsy devices have worked well, it is still to desired to provide an enhanced gripping surface which enhances the feel for a user of the instrument, while at the same time preventing slipping of a hand or fingers which grasp the handle portion of the instrument. It is likewise desired to provide an enhanced gripping surface which works well in condition where water, perspiration or other fluid may be present.

It is further desired to provide a bone marrow biopsy device with a handle having a cushioned gripping portion. In particular, many bone marrow biopsy devices must inherently be forced by a physician for insertion into a patient's bone, thus mandating a firm, tight grip on the handle of the instrument. It is beneficial to provide a softer, cushioned surface to alleviate some of the stress placed on the physician's hand.

It is also desirable to provide a bone marrow biopsy device with a handle which is easily molded, and which includes inserts which add to the weight of the handle and improve weight distribution throughout the handle. It is likewise desirable to provide an inexpensive, easily positioned insert which contributes to a comfortable handle weight, while also enhancing the grip of the handle.

It is also desired to provide a bone marrow biopsy device with a gripping surface which enhances the secured, locking relationship of the outer cannula handle portion to the inner rod handle portion, to facilitate simultaneous use of the outer cannula in conjunction with the inner rod, for insertion, manipulation, and removal of the bone marrow biopsy device from a patient.

These and other objects of the present invention will become apparent in light of the present specification, claims and drawings.

SUMMARY OF THE INVENTION

The present invention is directed to a bone marrow biopsy needle including an outer cannula and an inner rod. The outer cannula includes a proximal end, a distal end, a hollow section therebetween and a handle portion associated with the proximal end. The handle portion further includes a front portion, a rear portion, a top portion, a bottom portion and a grip enhancement member which is formed from a material distinct from at least a portion of the handle portion.

In a preferred embodiment, the grip enhancement member comprises at least one tactile insert member. The at least one tactile insert member preferably fits into at to least one corresponding cavity in the handle portion of the outer cannula. In one embodiment, handle portion includes cavities in both the front and rear portions, both of which contain separate front and rear tactile insert members. In another embodiment, the front portion includes two separate cavities, each of which include separate tactile inserts.

In a preferred embodiment, the at least one tactile insert member is constructed from rubber. The rubber provides a non-slip gripping surface, while enhancing gripping ability under wet conditions, such as those generated by a perspiring palm or other liquids in the surgical environment. The grip enhancement member also provides cushioning for a user and adds weight to the handle portion to facilitate weight distribution throughout the outer cannula handle.

In another preferred embodiment, the at least one insert member is constructed from other, preferably heavier materials, to add additional weight to the handle portion of the outer cannula.

In one embodiment, the grip enhancement member comprises a single piece extending from a front portion cavity, across at least a portion of the bottom portion, and into a back portion cavity. In another embodiment, the grip enhancement member comprises a tactile overlay attached to one or both of the front and rear portions of the handle portion of the outer cannula.

The inner rod includes a proximal end, a distal end and a handle cap. The inner rod may take the form of a sharpened stylet, an inner cannula, an ejector rod, or other solid or hollow rods. The handle cap is preferably associated with the proximal end of the inner rod, and is capable of securable engagement with the handle portion of the outer cannula to facilitate simultaneous insertion of the outer cannula and the inner rod into and removal from a patient.

In a preferred embodiment, the grip enhancement member extends outwardly beyond the handle portion to enhance the secured engagement of the outer cannula with the inner rod when the handle cap is positioned over the handle portion of the outer cannula in a locking orientation.

In another preferred embodiment, the handle cap includes a separate locking member for releasably locking the handle cap onto the handle portion of the outer cannula. In yet another preferred embodiment, the handle cap includes an alignment member for alignment with an orientation indicia on the handle portion of the outer cannula for directing proper orientation of the handle cap onto the handle portion.

BRIEF DESCRIPTION THE DRAWINGS

FIG. 1 is an exploded perspective view of the bone marrow biopsy device according to the present invention;

FIG. 2 is a perspective view of the bone marrow biopsy device as shown in FIG. 1, with the handle cap in a locked orientation relative to the handle portion of the outer cannula;

FIG. 3 is a fragmentary exploded perspective view of the handle portion of the outer cannula of the bone marrow biopsy device shown in FIG. 1;

FIG. 4 is a front elevational view of a portion of the bone marrow biopsy device shown in FIG. 1;

FIG. 5 is a side elevational view of a portion of the bone marrow biopsy device shown in FIG. 1;

FIG. 6 is a rear elevational view of a portion of the bone marrow biopsy device shown in FIG. 1;

FIG. 7 is a perspective view of the handle portion of the bone marrow biopsy device according to another embodiment of the invention; and FIG. 8 is an exploded perspective view of the handle portion of the bone marrow biopsy device according to yet another embodiment of the present invention.

DETAILED DESCRIPTION OF THE INVENTION

While this invention is susceptible of embodiment in many different forms, there is shown in the drawings, and will herein be described in detail, one specific embodiment with the understanding that the present disclosure can be considered as an exemplification of the principals of the invention and is not intended to limit the invention to the embodiments illustrated.

Bone marrow biopsy device 20 is shown in FIGS. 1–6 as comprising outer cannula 22 and inner rod 24. At the outset, while the present invention will be described in the specific context of a bone marrow biopsy device, the invention is certainly not limited to just bone marrow biopsy instruments. Indeed, the present invention may be used in conjunction with a multitude of medical or other instruments. Likewise, the present invention is effective for use in not only bone marrow biopsy retrieval procedures, but also with other instruments to perform other tissue retrieval procedures, other procedures involving the aspiration and/or injection of fluids or other materials through a instrument handle, or even other procedures and associated instruments as would be known by those of ordinary skill in the art with the present disclosure before them. Throughout this detailed description, like reference numerals will be used to designate like parts.

Also at the outset, while inner rod 24 is shown in the drawings as comprising a sharpened stylet or obturator used for cutting through soft and hard bone tissue, inner rod 24 may likewise comprise a hollow inner cannula used for sampling bone marrow tissue, an ejector rod for forcing that tissue from that outer cannula, as well as other types of inner rods well known by those of ordinary skill in the art with the present disclosure before them. Certain inner rod structures are disclosed in Mittermeier, Ser. No. 09/137,854, incorporated herein by reference.

Outer cannula 22, shown in FIGS. 1–6, includes cylindrical tube portion 30 and handle portion 32. Cylindrical tube portion 30 includes both proximal end 34 and distal end 36. Distal end 36 is shown in FIGS. 1 and 2 as having saddle point configuration 38 with sharp edges. Such a configuration, as is well known in the art, facilitates cutting through both soft and hard tissue, thus facilitating the entry of the bone marrow biopsy device into a bone marrow sampling region. However, it is likewise contemplated that other distal end point configurations may likewise be utilized with the present invention, depending on the specific biopsy application. Moreover, distal end 36 of cylindrical tube portion 30 may likewise include an inner tapered portion to facilitate bone marrow retrieval, such as disclosed in Mittermeier, Ser. No. 09/137,854.

Handle portion 32 is shown in FIGS. 1–6 as including aperture 40, connecting tube 42, top portion 44, bottom portion 46, front portion 48, rear portion 50, first side portion a 52, second side portion 54, front tactile insert member 56 and rear tactile insert member 58. Aperture 40 connects cylindrical tube portion 30 with connecting tube 42, which includes ridge 59 to facilitate locking of inner rod 24 to outer cannula 22, as will be described in more detail below. Ridge 59 may comprise a threaded region, such as that shown in FIGS. 4 and 6, or any other contoured portion which facilitates receipt of inner 20 rod 24.

Top portion 44 includes notch 60 and sloping portions 62 and 64. Notch 60, best seen in FIGS. 4 and 6, permits connecting tube 42 to exit aperture 40 of handle portion 32. As can be seen from the drawings, notch 60 is preferably off-center relative to connecting tube 42, so as to provide a larger space on one side of the connecting tube. Sloping portion 62 and 64 preferably extend from top portion 44 down to side portions 52 and 54, and facilitate a contoured fit of handle cap 122 onto handle portion 32.

Bottom portion 46 preferably includes finger grooves 66 and 68. The finger grooves facilitate grasping of handle portion 32 by a physician. However, while finger grooves 66 and 68 are certainly preferred, handle portion 32 may likewise be rounded or squared on bottom portion 46 without any finger grooves or special receptacles for a user's fingers.

Front portion 48, shown in FIGS. 1–5, includes first cavity 70, second cavity 72, To outer peripheral ridge 74 and barrel portion 76. First cavity 70 and second cavity 72, as can be seen in FIG. 3, are positioned on either side of barrel portion 76, which further includes orientation indicia 78. As can be seen in the drawings, orientation indicia 78 helps a user distinguish between the front and rear sides of bone marrow biopsy device 20, so as to properly indicate the orientation of distal end 36 of outer cannula 22 and/or the orientation of inner rod 24, for instance in those applications where the inner rod comprises a sharpened stylet. Moreover, while orientation indicia 78 is shown in the drawings as comprising a stepped arrow, any orientation indicia may be used in conjunction with the present invention as would be known by those with ordinary skill in the art with the present disclosure before them. Outer peripheral ridge 74 forms a wall 20 around first cavity 70 and second cavity 72.

Rear portion 50, shown in FIGS. 3, 5 and 6, likewise includes first cavity 80, second cavity 82, outer peripheral ridge 84 and a barrel portion (not shown, but preferably similar to barrel portion 76 on front portion 48, without an orientation indicia). Like first 70 and second 72 cavities in front portion 48, first cavity 80 and second cavity 82 are separated by the barrel portion, and enclosed by outer peripheral ridge 84.

Front tactile insert member 56 is shown in FIGS. 1–5 as including first front insert 90 and second front insert 92. Front tactile insert member 56 preferably comprises a rubber material which can easily be formed to fit the dimension, contour and shape of first cavity 70 and second cavity 72 of front portion 48 of handle portion 32. To this end, first front insert 90 and second front insert 92 are tailored to the contour and shape of first cavity 70 and second cavity 72, respectively, to preferably ensure an interference fit. Such a fit is preferably facilitated by the gripping nature of the rubber material, which permits secured positioning of the first front insert and the second front insert into first and second cavities 70 and 72, respectively. Furthermore, such an interference fit eliminates the need for use of adhesives or other securing materials, which materials not only add to the cost of manufacturing bone marrow biopsy device 20, but also may constitute an unwanted element in a typically sterile, surgical environment. However, it is likewise contemplated that an adhesive or other securing material may be used with first and second front inserts 90 and 92 to enhance their secured placement in first and second cavities 70 and 72.

As is shown in FIG. 5, first front insert 90 and second front insert 92 further include peaks 91 and 93, respectively, while rear tactile insert member 58 includes peak 99. Preferably, peaks 91 and 93 correspond to peak 53 in first side portion 52, while peak 99 corresponds to peak 55 in second side portion 54. As will be described below, peaks not only provide a stop for handle cap 122 on inner rod 24, but also enhance the locking relationship of handle cap 122 onto handle portion 32 of outer cannula 22.

Preferably, and as is shown in FIG. 5, first front insert 90 and second front insert 92 extend out of first cavity 70 and second cavity 72 beyond outer peripheral ridge 74. This ensures that a user grips the portion of handle 32 which includes the tactile insert surface. Furthermore, as is shown in FIGS. 1–4, first front insert 90 and second front insert 92 preferably frame orientation indicia 78, to leave the indicia exposed to a user. However, it is certainly contemplated that front tactile insert member 56 may, like rear tactile insert 58, comprise a single piece extending over barrel 76 and orientation indicia 78, if the indicia is not desired and/or necessary.

Rear tactile insert member 58, shown in FIGS. 3, 5 and 6, comprises first wing 94, second wing 96 and connecting portion 98. Like front tactile insert member 56, rear tactile insert member 58 is preferably constructed from a rubber polymer material. However, it is likewise contemplated that rear tactile insert member 58 may be divided into two separate and distinct inserts, such as first front insert 90 and second front insert 92. Rear tactile insert member 58 is likewise preferably positioned and releasably secured in first cavity 80 and second cavity 82 of rear portion 50 by an interference fit, generated by the rubber-on-plastic contact of rear tactile insert member 58 with the cavity walls of rear portion 50.

Constructing front tactile insert member 56 and rear tactile insert member 58 from rubber also provides increased cushioning for a physician during use of bone marrow biopsy device 20. In particular, the rubber material gives upon compression by a physician's fingers. Inasmuch as handle portion 32 is often clenched with a strong, tightened grip as the bone marrow biopsy device is forced into a patient's bone, clenching places a large amount of stress on a physician's hand. Allowing a portion of that stress to be dissipated through the cushioning rubber eases the tension and stress placed on a physician's hand. Moreover, the rubber construction likewise provides a non-slip, gripping surface for a physician. This is especially useful as stringent clenching of handle portion 24 may lead to perspiration in a physician's palm. Additionally, there may be potential moisture in the surgical environment. As is well known, rubber acts as an excellent gripping surface in wet conditions.

The same non-slip characteristic of rubber also prevents inadvertent sliding or displacement of bone marrow biopsy device 20 from a table or other resting surface. In particular, in a resting state bone marrow biopsy device 20 lies at least partially on either front portion 48 or rear portion 50. Inasmuch as front tactile insert member 56 and/or rear tactile insert member 58 preferably extend outwardly beyond front peripheral ridge 74 and/or rear peripheral edge 84, one of the insert members comes into contact with a resting surface. Thus, the gripping nature of the insert members prevent inadvertent slippage or displacement of the bone marrow biopsy device from the resting surface.

Aside from functioning to enhance the gripping surface of handle portion 32 of bone marrow biopsy device 20, front tactile insert member 56 and rear tactile insert member 58 also provide additional weight to handle portion 32. As is known in the art, many physicians prefer a weighted handle for purposes of feel and balance. The particular orientation and positioning of first front insert 90, second front insert 92 and rear tactile insert member 58 ensures that such a weight distribution is substantially uniform throughout handle portion 32, so as to maintain a consistent weighted feel of bone marrow biopsy device 20 during use. To this end, insert members 56 and 58 are preferably solid materials, such as rubber, which add density to handle portion 32. It is contemplated that the insert members may have a density substantially equal to or greater than that of the remainder of handle portion 32.

Additionally, it is likewise contemplated that front tactile insert member 56 and rear tactile insert member 58 may likewise be constructed from alternative materials, such as other plastics, polymers or even metals, to provide increased weight to handle portion 32. Of course, it is further contemplated that insert members 56 and 58 may be constructed from a combination of two materials to provide both weight and a tactile gripping surface. It is even further contemplated that two separate insert members may be used in association with each cavity, one insert member in the bottom of the cavity to provide weight, and a second insert member near the top portion of the cavities to provide a tactile gripping surface, or other combinations as would be known by those of ordinary skill in the art with the present disclosure before them.

The use of insert members, instead of a solid handle portion, provides even further advantages in the manufacturing of bone marrow biopsy device 20. In particular, those of ordinary skill in the art with the present disclosure before them will readily appreciate that the molding process favors those molds having a substantially constant wall thickness with various transitions. The constant wall thickness is preferably somewhat thinner than that typically required to form the entirety of a typical handle portion of a bone marrow biopsy needle. Indeed, the process of molding an overly thick, non-uniform handle portion may lead to shrinking, contortion and/or deformation of the handle portion. Accordingly, the use of one or more insert members allows handle portion 32 to be molded in a desirable, cost effective, efficient manner having a substantially constant wall thickness with suitable transitions, while at the same time providing the valuable additional weight desired by many physicians.

Of course, tactile insert members 56 and 58 are not necessarily limited to placement solely within cavities in front portion 48 and rear portion 50. As is shown in FIG. 7, bone marrow biopsy device 20' includes single tactile insert 100 having a rear portion, first front portion 104, second front portion 106, first underside connecting portion 108 and second underside connecting portion 110. First underside connecting portion 108 and second underside connecting portion 110 provide a tactile gripping surface in the finger groove in the bottom portion of handle portion 32'. Thus, an improved gripping surface, and its cushioning benefits, is provided in an area of handle portion 32' which may receive at least as much clenching force from a physician's hand —leading to further increased grip, prevention of slippage and increased cushioning.

Notably, first underside connecting portion 108 and second underside connecting portion 110 may be positioned directly over the bottom portion of handle portion 32'. However, and as is shown in FIG. 7, it is likewise contemplated that the outer peripheral ridges of the handle portion 32' may likewise include notches or paths specifically designed to accept first and second underside connecting portion 108 and 110. Furthermore, while shown as a single piece, tactile insert 100 may likewise comprise multiple insert member segments, as would be known by those in the art with the present disclosure before them.

In yet another embodiment, shown in FIG. 8, bone marrow biopsy device 20" includes a tactile overlay. In particular, solid handle portion 112 is shown without any cavities, but instead with front and rear handle surfaces 115 and 117, respectively, which receive first tactile overlay 114 and second tactile overlay 116. First and second tactile overlays 114 and 116 are preferably adhered to the front and rear handle surfaces 115 and 117 of solid handle portion 112 to provide a tactile gripping surface and cushioning to facilitate use of the bone marrow biopsy device. Of course, while not shown, the tactile overlay may be extended to the bottom of solid handle portion 112, as well as to the sides and/or top thereof—in one or multiple pieces.

Inner rod 24 is shown in FIGS. 1, 2 and 4–6 as comprising cylindrical rod portion 120 and handle cap 122. Cylindrical rod portion 120 includes proximal end 124 and distal end 126, and as discussed above, may comprise any number of desirable hollow or solid rods.

Handle cap 122 comprises front 130, rear 132, top 134, locking member 136 and alignment member 138. Front 130 preferably includes alignment indicia 140, which act in combination with orientation indicia 78 on handle portion 32 to indicate proper orientation of inner rod 24 within outer cannula 22. In particular, a user knows when as handle cap 122 is being positioned over handle portion 32 in a proper orientation when alignment indicia 140 corresponds to orientation indicia 78. Top 134 is shown in the drawings as having a substantially curved shape. This shape is desirable as it contours to the shape of a user's palm, which directly contacts top 134 during use of bone marrow biopsy device 20. However, it is likewise contemplated that the handle cap 122 in general, and top 134 more particularly, may comprise any shape as would be known by those of ordinary skill in the art with the present disclosure before them. Additionally, while not shown in the drawings, handle cap 122 may further include a tactile member, such as a tactile overlay, to enhance gripping and/or cushioning thereof. It is contemplated that such tactile member may be positioned on top 134, front 130 and/or rear 132 of handle cap 122.

Locking member 136 is shown in FIG. 1 as comprising gripping prongs 142 and 144. Gripping prongs 142 and 144 preferably engage ridge 59 on connecting tube 42 on handle portion 32. Locking member 136 ensures that handle cap 122 is secured to handle portion 32, to facilitate simultaneous insertion of outer cannula 22 and inner rod 24 into a patient.

Additionally, the secured locking relationship of handle cap 122 onto handle portion 32 of outer cannula 22 is enhanced by front tactile insert member 56 and rear tactile insert member 58. In particular, inasmuch as the insert members preferably extend beyond front peripheral outer ridge 74 and rear outer peripheral ridge 84, the inside of handle cap 122 preferably contacts a portion of insert member 56 and 58. Specifically, peaks 91 and 93 in front insert member 56 and peak 99 in rear insert member 58 are abutted by the inside surface of handle cap 122 to create an interference fit of handle cap 122 onto handle portion 32. This interference fit enhances the locking and secured relationship between handle cap 122 and handle portion 32, to facilitate simultaneous use of inner rod 24 and outer cannula 22.

Alignment member 138 is shown in FIG. 1 as comprising a shoulder. Alignment member 138 preferably fits into notch 60 in top portion 44 of handle portion 32, but only if handle cap 122 is oriented over handle portion 32 in a manner in which alignment indicia 140 aligns with orientation indicia 78. In particular, alignment member 138 fits only into the wider portion of notch 60, thus precluding secured attachment of handle cap 122 onto handle portion 32 in an orientation where there is no alignment of the handle cap with the handle portion of the outer cannula. Thus, a physician is precluded from attaching inner rod 24 to outer cannula 22 improperly. Of course, while alignment member 138 is shown as a shoulder, such an aligning function may be performed in a number of ways as would be known by those of ordinary skill in the art with the present disclosure before them.

The foregoing description and drawings are merely to explain and illustrate the invention, and the invention is not limited thereto except insofar as the independent claims are so limited, as those skilled in the art with the present disclosure before them will be able to make modifications and variations therein without departing from the scope of the invention.

What is claimed is:

1. A bone marrow biopsy device comprising:
   an outer cannula having a proximal end, a distal end and a substantially hollow cross-section between said proximal and distal ends;
   said outer cannula having a handle portion associated with said proximal end thereof,
   said handle portion including a front portion, a rear portion, a top portion, a bottom portion and at least one grip enhancement member associated with at least one of said front, rear, top and bottom portions, at least a portion of said at least one grip enhancement member formed from a material distinct from at least a portion of said handle portion to facilitate handling and use of said bone marrow biopsy device.

2. The bone marrow biopsy device according to claim 1 wherein said at least one grip enhancement member includes at least one tactile insert member, said at least one tactile insert member being securably associated with at least a portion of said handle portion of said outer cannula.

3. The bone marrow biopsy device according to claim 2 wherein said at least one tactile insert member is at least partially constructed from rubber.

4. The bone marrow biopsy device according to claim 2 wherein at least one of said front and rear portions of said handle portion of said outer cannula includes at least one cavity, said at least one tactile insert member being positioned at least partially inside said at least one cavity.

5. The bone marrow biopsy device according to claim 4 wherein each of said front and rear portions includes at least one cavity, and wherein at least one tactile insert member is positioned at least partially in said at least one front portion cavity and in said at least one rear portion cavity.

6. The bone marrow biopsy device according to claim 4 wherein at least a portion of said at least one tactile insert member is associated with said bottom portion of said handle portion of said outer cannula.

7. The bone marrow biopsy device according to claim 6 wherein said at least one tactile insert member comprises a single piece extending from said at least one front portion cavity, across at least a portion of said bottom portion, and into said at least one rear portion cavity.

8. The bone marrow biopsy device according to claim 4 wherein said at least one tactile insert member is retained in said at least one cavity by an interference fit.

9. The bone marrow biopsy device according to claim 1 wherein said at least one tactile insert member is constructed from a material having a greater density than that of said handle portion to facilitate weight distribution within said handle portion of said outer cannula.

10. The bone marrow biopsy device according to claim 1 wherein said grip enhancement member includes a tactile overlay associated with at least a portion of said handle portion of said outer cannula.

11. The bone marrow biopsy device according to claim 1 further including:
    an inner rod having a proximal end and a distal end, said inner rod being slidable within said outer cannula,
    said inner rod having a handle cap associated with said proximal end thereof, said handle cap capable of securable engagement with said handle portion of said outer cannula to facilitate simultaneous insertion of said outer cannula and said inner rod into and removal from a patient.

12. The bone marrow biopsy device according to claim 11 wherein at least a portion of said grip enhancement member extends outwardly beyond at least a portion of said handle portion of said outer cannula to enhance the secured engagement of said outer cannula with said inner rod when at least a portion of said handle cap is positioned over at least a portion of said handle portion of said outer cannula in a locking orientation.

13. The bone marrow biopsy device according to claim 12 wherein said grip enhancement member further includes an outer surface having a contour, said contour enhancing said secured engagement of said handle portion of said outer cannula with said handle cap of said inner rod when positioned in a locking orientation.

14. The bone marrow biopsy device according to claim 11 wherein said inner rod further includes a locking member for releasably locking said handle cap onto said handle portion of said outer cannula.

15. The bone marrow biopsy device according to claim 11 wherein said inner rod further includes an alignment member for directing proper orientation of said handle cap of said inner rod with said handle portion of said outer cannula.

16. The bone marrow biopsy device according to claim 11 wherein said grip enhancement member defines at least one alignment indicia, said alignment indicia directing proper orientation of said handle cap onto said handle portion when said inner rod is inserted into said outer cannula.

17. The bone marrow biopsy needle according to claim 1 wherein said inner rod comprises at least one of an inner cannula, a stylet, an obturator and an ejector rod.

18. The bone marrow biopsy device according to claim 1 wherein said handle portion further includes finger grooves to facilitate handling and use of said bone marrow biopsy device.

19. A method for forming a bone marrow biopsy device, said method comprising the steps of:
    attaching a handle portion to a proximal end of an outer cannula, said outer cannula having a proximal end, a distal end, a substantially hollow cross-section between said proximal and distal ends, and
    associating a at least one grip enhancement member, at least a portion of said grip enhancement member formed from a material distinct from at least a portion of said handle portion, with said handle portion of said outer cannula.

* * * * *

UNITED STATES PATENT AND TRADEMARK OFFICE
CERTIFICATE OF CORRECTION

PATENT NO. : 6,302,852 B1
DATED : October 16, 2001
INVENTOR(S) : Fleming, III et al.

It is certified that error appears in the above-identified patent and that said Letters Patent is hereby corrected as shown below:

Column 4,
Line 21, after "inner", delete "20"
Line 40, before "outer", delete "To"
Line 55, after "wall", delete "20"

Column 7,
Line 48, after "when", delete "as"

Signed and Sealed this

Tenth Day of September, 2002

Attest:

JAMES E. ROGAN
Attesting Officer    Director of the United States Patent and Trademark Office